United States Patent [19]

Horsey

[11] 4,013,019
[45] Mar. 22, 1977

[54] DRIVE FOR TILTABLE X-RAY TABLE

[75] Inventor: William Charles Horsey, Towson, Md.

[73] Assignee: CGR Medical Corporation, Baltimore, Md.

[22] Filed: Nov. 25, 1975

[21] Appl. No.: 635,049

[52] U.S. Cl. .............................. 108/5; 250/439 P; 269/323

[51] Int. Cl.² .......................................... A47F 5/12

[58] Field of Search .................... 108/4–8; 74/393; 248/343–395; 250/439, 444, 453, 456, 491; 269/323; 297/362

[56] References Cited

UNITED STATES PATENTS

| | | | |
|---|---|---|---|
| 2,534,623 | 12/1950 | Pitts et al. .................... | 250/439 X |
| 2,680,046 | 6/1954 | Stava .............................. | 108/8 UX |
| 2,816,806 | 12/1957 | Zaalberg ............................ | 269/323 |
| 2,872,584 | 2/1959 | Schiring et al. ................... | 250/444 |
| 3,131,301 | 4/1964 | Barrett et al. ..................... | 250/439 |
| 3,525,308 | 8/1970 | Koopmans .............. | 108/8 |
| 3,656,362 | 4/1972 | Buchsteiner ......................... | 74/393 |
| 3,823,617 | 7/1974 | Infanger et al. .................. | 74/393 X |

FOREIGN PATENTS OR APPLICATIONS

| | | | |
|---|---|---|---|
| 723,572 | 2/1955 | United Kingdom ............... | 250/444 |

Primary Examiner—Roy D. Frazier
Assistant Examiner—William E. Lyddane
Attorney, Agent, or Firm—Brady, O'Boyle & Gates

[57] ABSTRACT

To overcome floor clearance problems, a tiltable X-ray table is tilted at an accelerated rate between level and upright positions by a variable ratio positive gear drive. Simultaneously the table is caused to translate at a constant or linear rate by primary drive means mounted directly on the movable table body or chassis. Thus, the ratio of table body translation to tilt is greater at the beginning of table body travel than at later stages of travel. Table body translation is effected by twin ball nut screw shaft assemblies carried by opposite sides of the table body or chassis.

11 Claims, 9 Drawing Figures

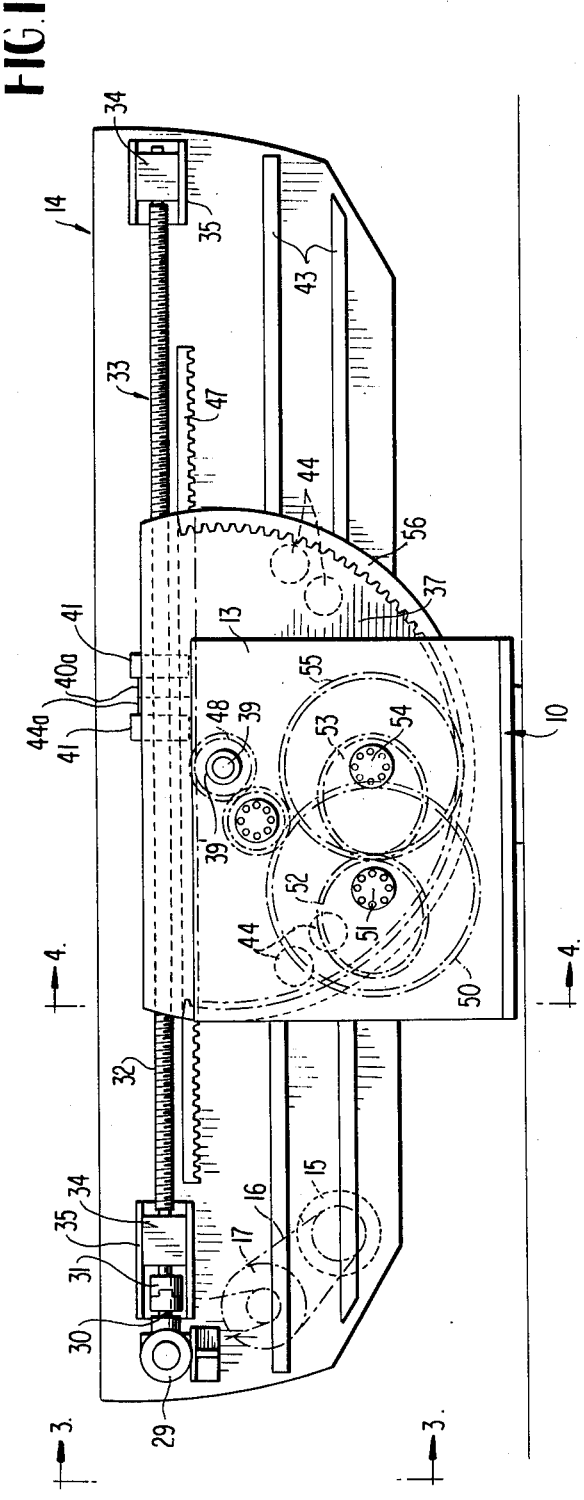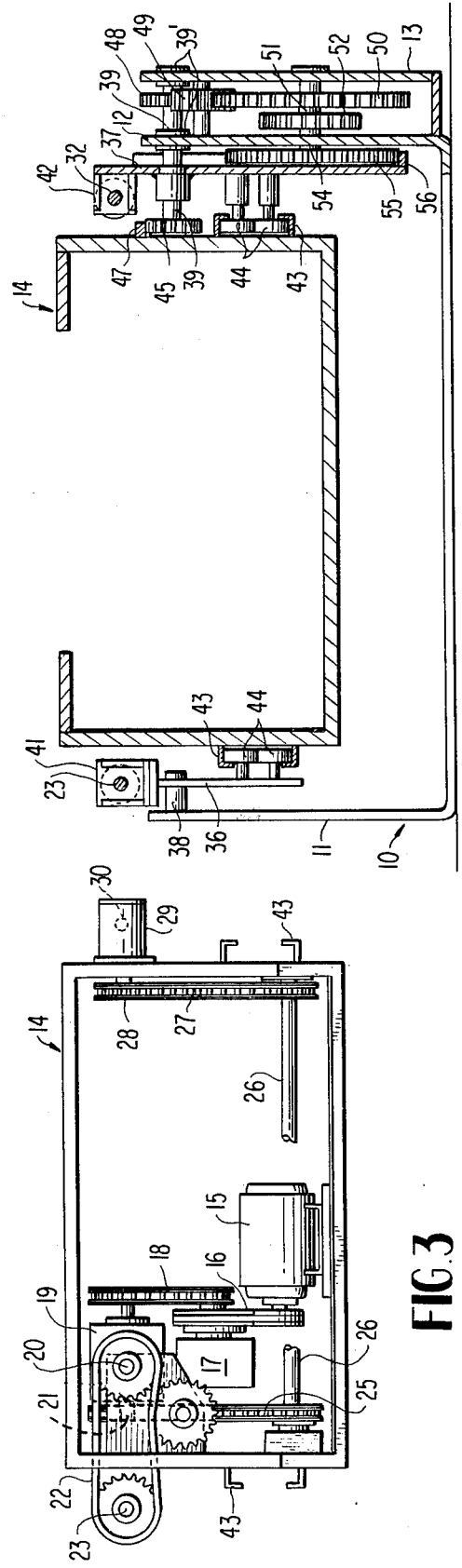

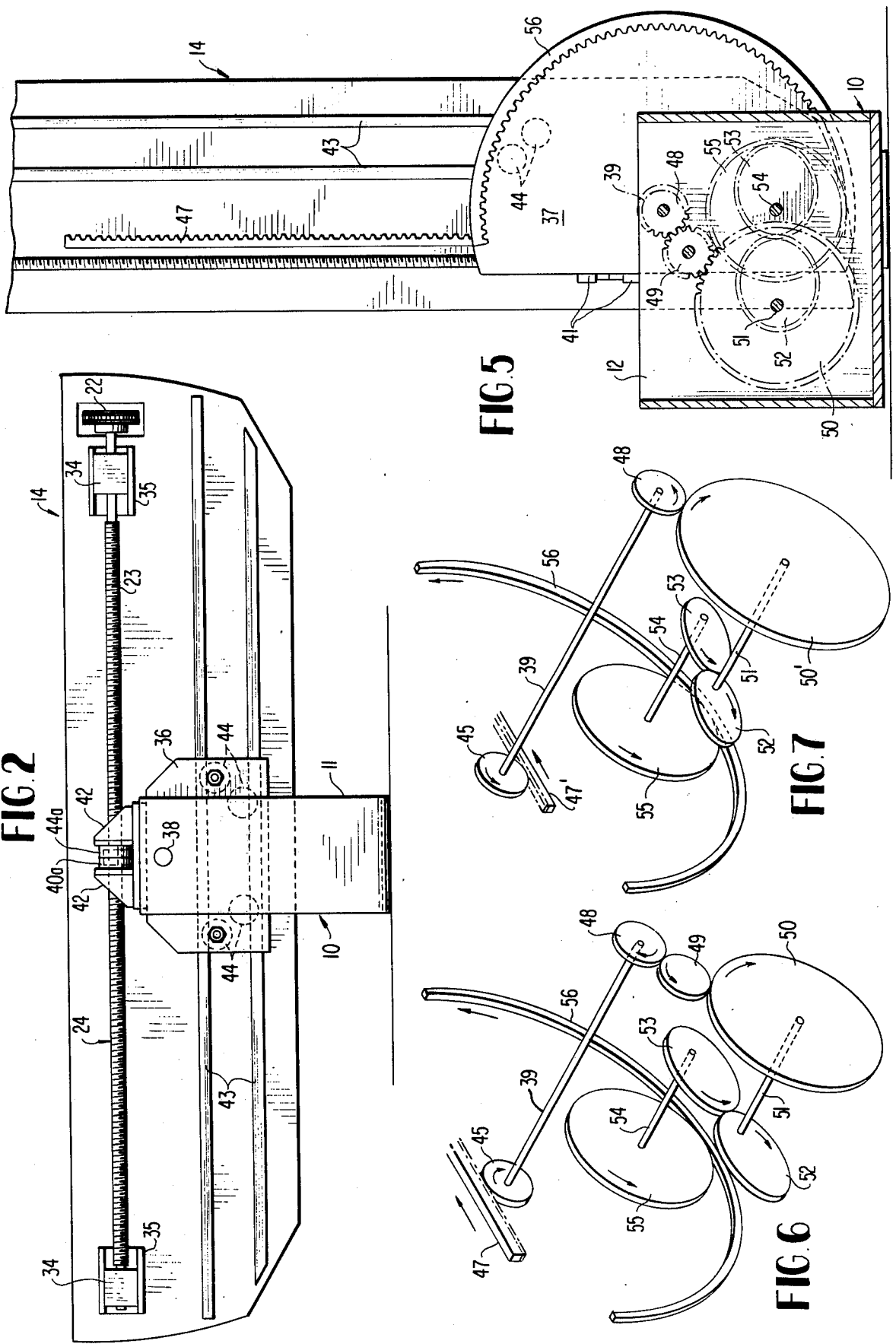

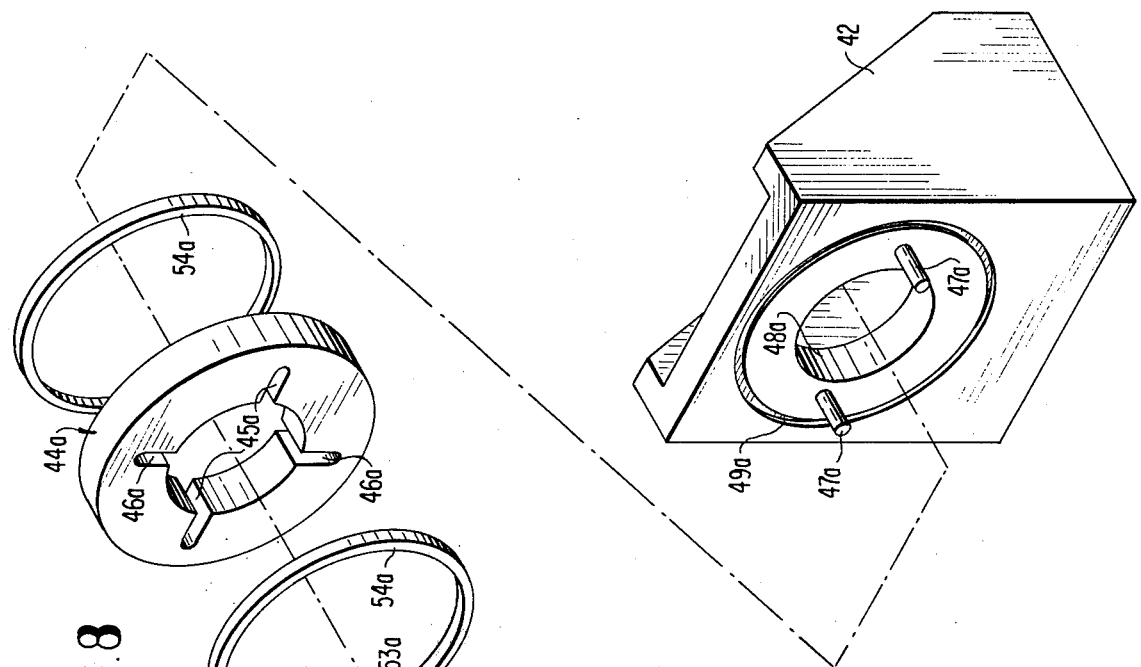
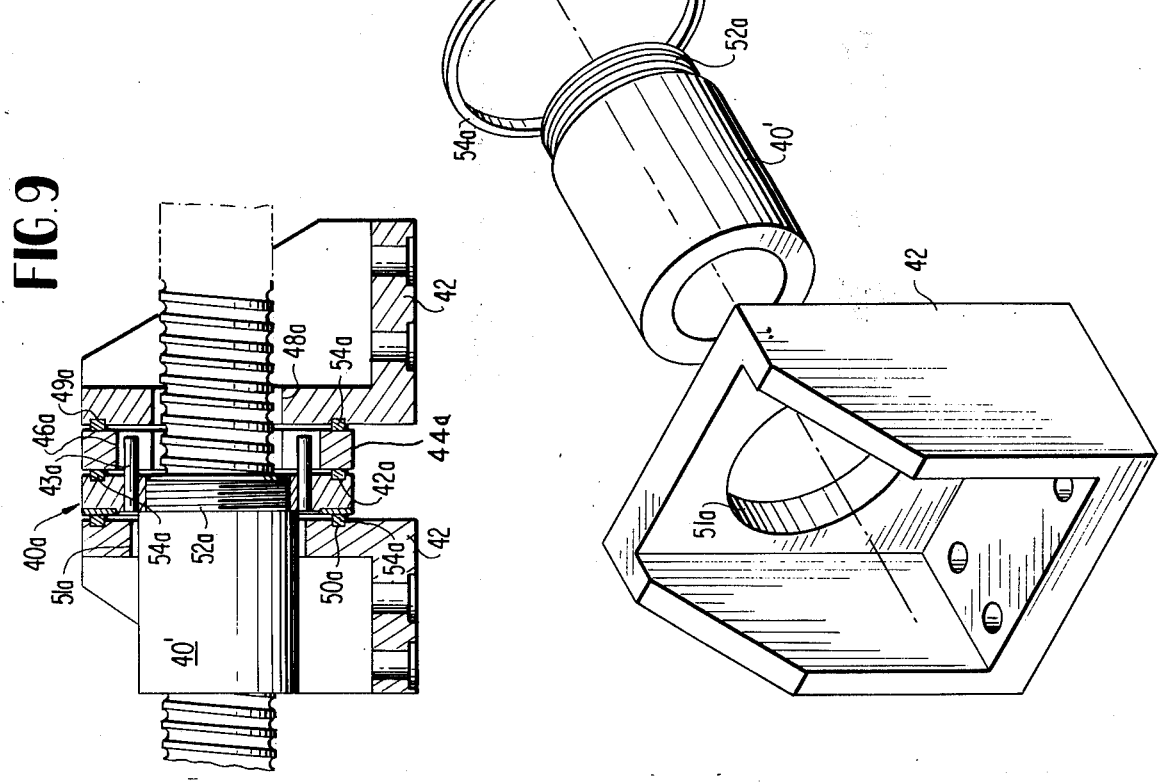

DRIVE FOR TILTABLE X-RAY TABLE

BACKGROUND OF THE INVENTION

It has been recognized in the prior art that, in order to maintain the tiltable bodies of X-ray examination tables at acceptable heights above the floor and to avoid floor interference problems during tilting, the table body or chassis must be driven in such a way that it will translate while its angularity is being changed from the horizontal toward the vertical and vice-versa. At least one prior art proposal provides for tilting and translatory movement of the X-ray table body at different and changing rates, and more particularly with the rate of translation of the table body taking place at a relatively high speed at the beginning of the tilting operation while tilting movement occurs at a uniform rate. With this technique, the table body is quickly shifted translationally out of the way to obtain the necessary floor clearance. U.S. Pat. No. 3,131,301 to Barrett et al. discloses this mode of operation. A somewhat similar arrangement is present in U.S. Pat. No. 3,525,308 to Koopmans. An earlier U.S. Pat. No. 2,816,806 discloses drive means to shift an X-ray examination table body in translation and in rotation simultaneously at constant or linear rates. A further example of the patented prior art is shown in U.S. Pat. No. 2,872,584 to Schiring et al. Generally speaking, the prior art arrangements for driving tiltable X-ray tables have not been entirely satisfactory in that they have tended to be unduly complex and costly and have lacked desirable compactness for commercial application. Customarily, in the prior art, the primary driving means for the adjustable table body has been located entirely within the floor pedestal of the table and not in the table body or chassis. A much more compact and uncluttered construction is achieved by the present invention by having the primary table driving means located within one end portion of the table body or chassis and away from the pedestal.

A primary problem encountered with the arrangement proposed by the Barrett et al. patent arises as a result of the use of a sheave and cable drive means to achieve a variable rate of translation for the table body. The cable means will inevitably stretch during continued use, making it very difficult to maintain the correct tilt to translation ratio during operation. This difficulty is completely solved in the present invention by the employment of positively operating variable ratio drive gearing for tilting the table body at a non-linear or non-uniform rate while translational movement occurs at a constant rate. More particularly, in the invention, a pair of elliptical gears are utilized in the tilt or table angularity drive system to produce a relatively slow rate or tilt at the beginning of table body movement and to gradually increase the tilting rate to a maximum rate as the table body reaches the upright or vertical position. Not only does the positive drive of the invention avoid the use of flexible transmission elements which are subject to stretch and springiness, but in so doing provides for the essential floor clearance requirement during table tilting by an improved and more reliable mode of operation.

SUMMARY OF THE INVENTION

In achieving the general objective of improvement of the known prior art through a more compact, positive acting, efficient and reliable table drive, the invention may be summarized as follows.

The primary drive means for the tiltable table body including drive motor, fail safe electrical brake, and associated transmission gearing leading to twin ball nut and screw shafts is housed in one end portion of the table body or chassis. The twin parallel ball nut and screw shaft assemblies journaled on opposite sides of the table body and coupled with the aforementioned primary drive means to be driven thereby in unison to effect table body translation. The table body is guided in its translatory movement by opposite side track means which engages pedestal mounted guidance and support rollers which are carried by pivotal mounting members suspended on the table pedestal.

The nut components for the ball nut and screw shafts are constrained through the relatively stationary pedestal from translating with the table body while being adapted to pivot with said pivotal mounting members around the tilt axis of the table body.

A rack gear attached to one side of the table body and translating therewith forces rotation of a train of gears mounted on one side of the floor-mounted pedestal. This train of gears includes the two elliptical gears whose operation imparts the varying and increasing rate of tilting motion to the table body as the latter moves from a level to an upright position with a uniform rate of translatory motion. The gear train embodying the elliptical gears also includes an output bull gear on the adjacent pivotal mounting member which can rotate on the tilt axis of the table body. Consequently, the table body is forced to rotate or tilt when the bull gear is turned, and table body tilting and translation occur simultaneously.

BRIEF DESCRIPTION OF DRAWINGS

FIG. 1 is a side elevation of an X-ray examination table embodying the invention in a level attitude;

FIG. 2 is an opposite side elevation thereof;

FIG. 3 is an end elevational view of the table body or chassis depicted in FIG. 1 and taken on line 3—3 of FIG. 1;

FIG. 4 is a transverse vertical section taken on line 4—4 of FIG. 1;

FIG. 5 is a side elevational view, partly in section, showing the tiltable examination table in a full upright position;

FIG. 6 is a partly schematic perspective view of variable ratio gearing employed for the tilt drive of the table body;

FIG. 7 is a similar view showing a modification of the gearing;

FIG. 8 is an exploded perspective view of a self-alignment support means for the ball nut of a ball nut and screw shaft assembly; and FIG. 9 is an assembled cross sectional view through the means shown in FIG. 8.

DETAILED DESCRIPTION

Referring to the drawings in detail, wherein like numerals designate like parts, the numeral 10 designates a floor-mounted stationary pedestal having spaced opposed upstanding sides 11 and 12. As shown in FIG. 4, an additional fixed vertical wall 13 is provided on the pedestal or base 10 outwardly of and parallel to the side 12 to form a protected chamber for drive gearing yet to be described.

An X-ray examination table body or chassis 14 is mounted between the sides 11 and 12 of the pedestal 10 for combined tilting and translatory movement between the level position shown in FIG. 1 and the full upright position of FIG. 5, where the table body has traveled 90° from the horizontal responsive to the operation of drive means and suspension means forming the particular subject matter of this invention.

The primary power drive means or gearing for table body 14 is conveniently contained in and supported on the table body near one end thereof, as shown particularly in FIGS. 1 and 3. Referring to these figures, an electric drive motor 15 based on the bottom wall of table body 14 has its output shaft connected through belt transmission means 16 with a conventional fail safe electric brake 17 whose shaft is connected by chain and sprocket gearing 18 to a first right angular gear box 19 having first and second output shafts 20 and 21. The output shaft 20 of gear box 19 is connected by further chain and sprocket gearing 22 to a screw shaft 23 of a first ball nut and screw shaft assembly 24 adjacent one side wall of the table body 14 and extending lengthwise thereof near the top of the table body, as will be further described. The second output shaft 21 of gear box 19 drives additional chain and sprocket gearing 25 extending downwardly in the table body and operatively connected with and driving a lower transverse drive shaft 26 journaled for rotation near the bottom wall of the table body.

Near the far side of table body 14, FIG. 3, the shaft 26 drives upwardly extending chain and sprocket gearing 27, coupled with the input shaft 28 of a second right angular gear box or drive 29 having an output shaft 30 coupled as at 31, FIG. 1, with a screw shaft 32 of a twin parallel ball nut and screw shaft assembly 33 adjacent the side wall of the table body 14 which is remote from the previously-mentioned screw shaft assembly 24.

The twin screw shafts 23 and 32 are driven in synchronism by the primary power drive means or gearing described immediately above in connection with FIG. 3. The opposite ends of both parallel screw shafts are mounted for rotation by journal elements 34 held in journal brackets 35, suitably anchored to the vertical side walls of the tiltable table body 14.

Pivotal suspension plates 36 and 37 adapted to swing in vertical planes are pivotally mounted, respectively, on coaxial pivot elements or shafts 38 and 39, secured to side walls 11, 12 and 13, as best shown in FIG. 4. The two coaxial elements 38 and 39 define the transverse rotational or tilt axis of the table body 14 on which the latter turns in a vertical plane while moving to or from its level or upright positions in accordance with the invention. Pivot element 38 may be rigid with pedestal side wall 11, whereas shaft 39 is rotatably supported in bearing means 39' on the two walls 12 and 13 and forms the power input shaft of a variable ratio gear train, to be described.

Referring particularly to FIGS. 8 and 9, the invention further comprises floating or self-aligning support means for the nuts 40' of the ball nut and screw shaft assemblies 24 and 33. The support means includes support extensions 41 and 42, secured rigidly to the tops of pivotal suspension plates 36 and 37, respectively. A first floating collar 40a is provided, having a central threaded bore 41a and an annular groove 42a in its interior face. A pair of diametrically opposed guide pins 43a are secured rigidly to the floating collar 40a and project beyond the interior side thereof outwardly of the threaded bore 41a and inwardly of the groove 42a. A second floating collar 44a has a first diametrically aligned pair of internal notches 46a in a vertical plane receiving the pins 43a for self-alignment in one plane. A second pair of diametrically aligned internal notches 45a in the floating collar 44a receive horizontal diametrically aligned projecting pins 47a secured rigidly to the support extension 42, such support extension also having a central screw shaft clearance opening 48a and a concentric groove 49a in its forward face, somewhat outwardly of the pins 47a. Similarly, the opposing support extension 42 has an annular groove 50a in its forward face and a central concentric shaft clearance bore 51a, as shown in the drawings.

A threaded extension 52a on one end of the ball nut 40' is received in the threaded bore 41a of floating collar 40a and secured rigidly by a radial set screw 53a. Three thrust rings 54a preferably formed of teflon impregnated bronze bonded to steel or equivalent material are seated in the grooves 42a, 49a and 50a, as shown in FIG. 9 with the opposite faces of the thrust rings slidably engaging ungrooved faces of the two collars 40a and 44a. The grooves prevent slipping of the steel surfaces of the thrust rings and allow slipping only on their low friction surfaces which contact the ungrooved faces of the two floating collars. The assembled relationship of the components in FIG. 8 is shown in FIG. 9. While the description relative to FIG. 8 was specific to the ball nut and screw shaft assembly 24 shown in FIG. 2, it is to be understood that the identical support structure is employed with the assembly 33 on the opposite side of the table as shown in FIG. 1.

The necessity for the self-aligning support means for the ball nuts 40' arises as a result of some inevitable waviness in the sheet metal of the table body 14 and some irregularities in the track and roller guide means for the table body, yet to be described. As the table body 14 translates past the described ball nut support means, such means compensates automatically for any misalignment and prevents severe side loading or binding of the ball nut and screw shaft assemblies 24 and 33. Lateral realignment takes place automatically in the support means because of the ability of the two floating collars 40a and 44a to shift laterally in either of two right angular planes due to the described engagement of the pins 43a and 47a in the respective adjustment notches 45a and 46a. This sidewise adjustment of the ball nuts 40' is entirely automatic during operation of the two screw shaft assemblies. It does not interfere with the normal translatory movement of the table body 14 by the screw shafts. In fact, the floating support arrangement renders table body translation smooth and entirely free of binding, despite lateral tolerance variations which are inevitably present.

It will be understood that the set screw 53a which locks the floating collar 40a to ball nut 40' prevents rotation of the ball screw nut (due to torque) relative to the support extensions 41 and 42, because the two sets of pins 43a and 47a are interlocked to allow horizontal and vertical shift but not rotation of the ball nuts. Thus, a means to restrain rotation of the ball nuts is provided in the mechanism.

Linear guide tracks 43 for the table body 14 are suitably fixed to both side walls thereof below the elevation of journal brackets 35 and associated parts. Pairs of support and guidance rollers 44 on the suspension plates 36 and 37 have supportive guiding engagement with the tracks 43 and allow freedom of translation of the table body relative to the pedestal 10 while simultaneous tilting or rotation is being imparted to the table body at a variable rate by gearing which will be described. The guide track and roller construction for the table body is shown somewhat schematically in the drawings for the sake of simplicity. In actual practice, the guide track arrangement affords positive linear and lateral guidance for the table body 14 during translation by the provision of different sets of rollers arranged for guidance of the table body in two planes, that is, longitudinally and laterally.

The variable ratio gearing forming the essence of the invention comprises a pinion or power input gear 45 close to one side wall of the table body 14, FIG. 4, and carried by the rotational shaft 39. The shaft 39 serves the dual purpose of forming a rotational element of the gear train shown in FIGS. 4 and 6 and also forming with the coaxial element 38 the main pivot axis for table body 14. A rack gear 47 or driver means attached fixedly to the adjacent vertical side wall of table body 14 meshes with pinion gear 45 and causes the same to rotate as the table body moves in translation under influence of screw shafts 23 and 32. A further gear 48 turns with the shaft 39 and is secured to this shaft between the walls 12 and 13. The gear 48 drives a similar direction reversing gear 49 of the gear train, in turn meshing with and driving a relatively large gear 50 on a rotational shaft 51.

The shaft 51 carries the first elliptical gear 52 of a pair of such gears employed in the table body tilting variable ratio gear train. The second elliptical gear 53 of like size is in mesh with the gear 52 and is mounted on another rotational shaft 54 carrying a larger spur gear 55, meshing with an internal toothed bull or ring gear 56 secured rigidly to the outer face of the adjacent pivotal suspension plate 37 and constituting the power output gear element of the variable ratio gear train. It may be noted that, with the X-ray table body 14 level or horizontal, the major axes of the two elliptical gears 52 and 53 are aligned. Consequently, tilting motion imparted to the table body by the elliptical gears in either of two directions will be symmetrical.

It should now be apparent that when translation of the table body 14 is caused by operation of the screw shafts 23 and 32 within their relatively stationary ball nuts 40, such translation and resulting movement of rack 47 powers the described pedestal mounted gear train through turning of pinion gear 45. The coacting guide tracks 43 and rollers 44 allow free translation of the table body 14, but these elements force rotation or pivoting of the table body about the main pivot axis 38–39 when the pivotal suspension plate 37 is rotated by the output gear 55 of the described gear train.

By observing the dispositions of the two elliptical gears 52 and 53 and their respective shafts 51 and 54 in FIGS. 1, 5 and 6, it will be understood that the driving elliptical gear 52 with the much shorter radius between its shaft 51 and the meshing teeth will impart rotation to the driven elliptical gear 53 at a substantially reduced rate of rotation, because of the longer radius between the meshing teeth of these two gears and the axis of shaft 54. In other words, with the major axes of the two elliptical gears coinciding as in FIG. 6, the driving gear 52 will initially function as a smaller diameter gear driving a much larger diameter gear with a resultant decrease in the speed of rotation of the driven gear. As a result, rotational movement of the table body 14 will initially be at a slow rate as translation of the table body begins at a constant rate. As the operation progresses, the two elliptical gears will progressively accelerate the rotation of the table body around the pivotal axis 38–39 while translation continues at the same rate. When the table body 14 is upright, FIG. 5, following a full 90° of rotation, the rate of angular rotation will be the maximum through the variable ratio gears 52 and 53. This can be seen in FIG. 5 where the relative positions of the shafts 51 and 54 are now reversed along the coincident major axes of the elliptical gears, compared to the positions of the shafts 51 and 54 in FIG. 6. In other words, referring to FIG. 5, the driving gear 52 now has the greater radius and the driven gear 53 the smaller radius so that the latter gear will be driven at increased speed rather than at decreased speed as in FIG. 6 when the table was level.

FIG. 7 shows a slight modification and simplification of the table tilting variable ratio positive gear drive wherein the direction reversal gear 49 may be eliminated. To accomplish this elimination of one gear, the rack gear 47' shown in FIG. 7 is caused to drive the bottom of pinion gear 45 rather than the top thereof, so as to impart reverse rotation to it as well as to the shaft 39 and gear 48. The gear 48 can then directly mesh with a larger gear 50' in the modified train carried by the shaft 51. All other elements of the gear train remain identical in construction and operation to the previously-described embodiment and therefore no further description to the simple modification of the variable ratio gearing is thought to be necessary. In either embodiment, the overall operational result is the same, namely, causing the tilting or angular rotation of the table body 14 to commence slowly during constant speed translation and to gradually accelerate and reach a maximum rate as the table body approaches the upright attitude. With this mode of operation, the table body with shift clear of the floor while tilting and it will not be necessary to greatly reduce the lower corner spaces of the table body.

With the primary power drive means housed inside of the table body, the overall bulk of the drive is greatly reduced in comparison to the prior art. Also the drive is direct and positive throughout with no possibility of slippage and no flexible elements subject to stretching involved, such as cables.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. An X-ray examination table comprising a relatively stationary pedestal and a movable patient supporting table body having a rotational axis, means supporting the table body on said pedestal and allowing the table body to move translationally and rotationally relative thereto, a primary power drive means connected with the table body to produce translational movement thereof, and a variable ratio gear train connected with the table body to move it with increasing angular velocity around said rotational axis of the table body during said translational movement of the table body by said primary power drive means, said table body carrying a driver means for said variable ratio gear train to power the gear train during said translational movement of the table body, said variable ratio gear train including a pair of engaging elliptical gears, and said elliptical gears having their major elliptical axes coinciding when the table body is in a level attitude, whereby rotational movement of the table body toward an upright attitude increases from a minimum angular velocity to a maximum angular velocity by operation of said gear train during said translational movement of the table body.

2. An X-ray examination table according to claim 1, and said first-named means comprising fixed axis rotational suspension means for said table body on said pedestal, and translational guide means for the table body interconnecting the same with said fixed axis rotational suspension means.

3. An X-ray examination table according to claim 2, and said fixed axis rotational suspension means including a rotary shaft also serving as the power input shaft for said gear train and being operatively coupled with said driver means of said table body.

4. An X-ray examination table according to claim 3, and a power input gear on said rotary shaft, said driver means comprising a rack gear fixed to one side of the table body and meshing with said power input gear.

5. An X-ray examination table according to claim 2, and said fixed axis rotational suspension means comprising fixed axis shaft means on said pedestal, side suspension plate elements for said table body rotatably attached to said shaft means, translational movement guide tracks for the table body secured to opposite sides thereof, and support and guidance roller means on said suspension plate elements engaged movably with said tracks.

6. An X-ray examination table according to claim 5, and a bull gear element on one side suspension plate element and forming the power output gear element of said variable ratio gear train, said bull gear element being coaxial with said fixed axis shaft means.

7. An X-ray examination table according to claim 1, wherein said primary power drive means is bodily mounted on said table body to move therewith in translation and rotation of the table body.

8. An X-ray examination table according to claim 7, and said primary power drive means comprising twin parallel ball nut and screw shaft assemblies carried by opposite sides of the table body and operatively coupled with said means supporting the table body on said pedestal, and powered drive gearing coupled with said twin screw shaft assemblied to turn the screw shaft elements thereof in unison.

9. An X-ray examination table according to claim 8, and means forming a part of said means supporting said table body on said pedestal and engaging the ball nuts of said ball nut and screw shaft assemblies and restraining the ball nuts from turning with the screw shaft elements, whereby the latter may travel axially relative to the ball nuts.

10. An X-ray examination table according to claim 1, and said primary power drive means including a constant speed motor means for producing translational movement of the table body at a constant rate.

11. An X-ray examination table according to claim 9, and said last-named means including a ball nut engaging floating support element which is self-aligning transversely of the screw shaft axes in two right angular planes normal to the screw shaft axes, whereby automatic compensation for side loadings on said screw shaft assemblies is enabled.

* * * * *